US007257991B2

(12) United States Patent
Wickstead et al.

(10) Patent No.: US 7,257,991 B2

(45) Date of Patent: Aug. 21, 2007

(54) SAMPLE TESTING DEVICE

(75) Inventors: James C. Wickstead, Mendham, NJ (US); Keith A. Seritella, Washington, NJ (US)

(73) Assignee: Rapid Medical Diagnostics Corporation, Miami Beach, FL (US)

( * ) Notice: Subject to any disclaimer, the term of this patent is extended or adjusted under 35 U.S.C. 154(b) by 192 days.

(21) Appl. No.: 10/618,796

(22) Filed: Jul. 14, 2003

(65) Prior Publication Data

US 2004/0014203 A1 Jan. 22, 2004

Related U.S. Application Data

(62) Division of application No. 10/046,528, filed on Jan. 14, 2002, now Pat. No. 6,634,243.

(51) Int. Cl.
*G01N 33/48* (2006.01)

(52) U.S. Cl. ...................... 73/64.56; 422/61; 73/61.43; 73/61.62

(58) Field of Classification Search ............. 73/863.23, 73/863.41, 863.71, 864.71, 864.73; 422/61, 422/57

See application file for complete search history.

(56) References Cited

U.S. PATENT DOCUMENTS 4,065,263 A * 12/1977 Woodbridge, III ........... 422/57
4,235,601 A 11/1980 Deutsch et al. ........... 23/230 R
4,299,916 A 11/1981 Litman et al. ................. 435/6
4,409,988 A 10/1983 Greenspan .................. 128/759
4,418,702 A 12/1983 Brown et al. ............... 128/760
4,580,577 A 4/1986 O'Brien et al. ............. 128/760
4,635,488 A 1/1987 Kremer ................... 73/864.72
4,774,962 A 10/1988 Hebel et al. ................ 128/760
4,820,399 A 4/1989 Senda et al. ................ 204/403
4,900,663 A 2/1990 Wie et al. ...................... 435/7
4,978,504 A 12/1990 Nason ......................... 422/61

(Continued)

FOREIGN PATENT DOCUMENTS

EP 0 187 167 A1 7/1986

(Continued)

OTHER PUBLICATIONS webpage @ http://www.salv.com/test.htm.

(Continued)

*Primary Examiner*—Hezron Williams
*Assistant Examiner*—Nashmiya Fayyaz
(74) *Attorney, Agent, or Firm*—Stroock & Stroock & Lavan LLP

(57) ABSTRACT

A sample testing device has a buffer container that can hold buffer fluid, a filter with a securement for holding a test strip, the test strip, a test strip container having a receptacle to accommodate the filter, so that when the filter is held therein the test strip is disposed in the receptacle, and a sample collector for holding a sample. The sample collector receives the buffer container, and the sample collector has a piercing member which, when the buffer container is placed in the sample collector, pierces the buffer container. Buffer fluid in the buffer container then contacts the sample. As buffer fluid flows through the sample collector, the buffer fluid that has contacted the sample passes through the filter to the test strip.

13 Claims, 13 Drawing Sheets

U.S. PATENT DOCUMENTS

| | | | | |
|---|---|---|---|---|
| 4,999,285 | A | 3/1991 | Stiso | 435/7.9 |
| 5,030,558 | A | 7/1991 | Litman et al. | 435/7.91 |
| 5,039,607 | A | 8/1991 | Skold et al. | 435/7.5 |
| 5,056,521 | A | 10/1991 | Parsons et al. | 128/635 |
| 5,121,856 | A * | 6/1992 | Weiler et al. | 222/209 |
| 5,141,850 | A | 8/1992 | Cole et al. | 436/525 |
| 5,260,031 | A | 11/1993 | Seymour | 422/101 |
| 5,268,148 | A | 12/1993 | Seymour | 422/101 |
| 5,283,038 | A | 2/1994 | Seymour | 422/101 |
| 5,376,337 | A | 12/1994 | Seymour | 422/101 |
| 5,380,492 | A | 1/1995 | Seymour | 422/101 |
| 5,393,496 | A | 2/1995 | Seymour | 422/101 |
| 5,477,863 | A | 12/1995 | Grant | 128/759 |
| 5,494,646 | A | 2/1996 | Seymour | 422/101 |
| 5,869,003 | A * | 2/1999 | Nason | 422/58 |
| 5,935,864 | A | 8/1999 | Schramm et al. | 436/174 |
| 6,375,897 | B1 * | 4/2002 | Bachand | 422/58 |
| 6,656,745 | B1 * | 12/2003 | Cole | 436/514 |
| 2001/0008614 | A1 | 7/2001 | Aronowitz | |
| 2001/0034068 | A1 | 10/2001 | Spivey et al. | |

FOREIGN PATENT DOCUMENTS

| | | |
|---|---|---|
| EP | 0 354 704 | 2/1990 |
| WO | WO88/08534 | 11/1988 |
| WO | WO90/14163 | 11/1990 |
| WO | WO91/13355 | 9/1991 |
| WO | WO93/09431 | 5/1993 |
| WO | WO95/11621 | 5/1995 |

OTHER PUBLICATIONS webpage @ http://www.salv.com/company.htm.
webpage @ http://www.salv.com/hema.htm.
webpage @ http://www.salv.com/pylori.htm.
webpage @ http://www.salv.com/serostrip.htm.
webpage @ http://www.salv.com/salivasampler.htm.

* cited by examiner

SAMPLE TESTING DEVICE

CROSS-REFERENCE TO RELATED APPLICATIONS

This application is a divisional of and claims priority under 35 U.S.C. § 120 of U.S. patent application Ser. No. 10/046,528 filed on Jan. 14, 2002, now U.S. Pat. No. 6,634,243 entitled SAMPLE TESTING DEVICE, which is herein incorporated by reference.

BACKGROUND OF THE INVENTION

1. Field of the Invention

The present invention relates generally to an apparatus for collecting, processing and analyzing a liquid specimen in a fully integrated system. This invention also relates to a method for collecting, processing, and analyzing a liquid specimen.

2. Description of the Related Art

Diagnostic testing throughout the world is currently carried out using a variety of different specimen types. Many of the samples tested, such as whole blood, serum, oral fluid, plasma, cerebrospinal fluid and others, are liquid.

Testing for infectious diseases under laboratory conditions typically involves use of a blood serum specimen obtained by removing the blood cells from an intravenous blood sample by centrifugation. The sample is first drawn from the patient by a trained phlebotomist. The serum sample so obtained is then tested under laboratory conditions using one of a number of methodologies, such as Enzyme Linked Immuno Sorbent Assay (ELISA), Immunofluorescence (IFA), Latex Agglutination (LA), or any of a number of automated instrument platforms employing chemiluminescence, fluorescence or other sensitive technologies. As there are other known diagnostic technologies in place, this is by no mean an exhaustive list.

Although serum testing under laboratory conditions has traditionally constituted the technique of choice, there is now a growing trend to move testing closer to the patient and use alternative specimen matrices such as whole blood and others. In other words, the sample is drawn from the patient, processed and analyzed more rapidly, often while the patient is still in attendance. The recent advance known as "near-patient" or "point-of-care" testing has caused a major shift in the way testing is done. Statistics show growth of over 20% per annum in this mode of testing for each of the last four years.

Such growth in this mode of testing has resulted in the increased use of alternate specimen types (e.g. whole-blood or oral fluid) not requiring the use of trained phlebotomists or additional steps to separate red blood cells from the required specimen. Rather, the sample can be drawn from the patient and processed directly. As a consequence, results can now be obtained, analyzed and conveyed to the patient while the patient or subject is still in the presence of the healthcare provider. This avoids the need for repeat patients or the need for the patient to contact the healthcare provider at a future time to obtain their test results.

Point-of-care (POC) testing therefore offers the advantage of giving the physician (and, if the physician chooses, the patient) immediate results, in contrast to conventional testing, where there is a waiting period, that could be anywhere from several hours to weeks, during which the specimens are transported to a laboratory testing facility, processed, and results sent to the physician.

It is standard in the industry to confirm infectious disease test results by repeat testing, often by a more sensitive methodology, especially when the testing is for potentially life-threatening diseases such as HIV, Hepatitis C, Hepatitis B, and so on. This applies regardless of whether the testing is performed in a laboratory or at the point-of-care. The second test used to confirm the result of the primary test is known as a "confirmatory" or "confirmation" test and typically uses a different methodology to confirm a diagnosis or otherwise. For instance in HIV diagnostics, Western Blot or ELISA methods may be used. In all instances a second specimen will be required. Owing to the serious nature of such testing, anything that can expedite sample processing is of tremendous importance.

In the case of laboratory testing, there may be sufficient specimen material remaining from the initial blood draw to carry out confirmation testing.

However, no rapid (in-office) tests are known which include a mechanism to collect a specimen for confirmatory testing at the time of the first patient visit to the healthcare facility.

SUMMARY OF THE INVENTION

The present invention is directed to a sample testing device having a buffer container that can contain buffer fluid therein, a filter having a securement for holding a test strip, the test strip, an end of which is held by the securement, a test strip container having a receptacle dimensioned and disposed to accommodate the filter, so that when the filter is held therein the test strip is disposed in the receptacle, and a sample collector for holding a sample.

In an embodiment, the sample collector is shaped to receive the buffer container, and the sample collector has a channeling member and a piercing member which, when the buffer container is placed in the sample collector, pierces the buffer container so that the buffer fluid in the buffer chamber contacts the sample and passes through the lumen to the filter. As buffer fluid flows through the lumen of the sample collector the buffer fluid that has contacted the sample passes through the filter to the test strip.

In a further embodiment, the sample collector has both a top and a bottom opening, wherein said top opening is shaped to receive said buffer container and said bottom opening is shaped to receive the filter. The sample collector also houses a piercing member which pierces the buffer container when the buffer container is placed in the top opening of the sample collector, thereby releasing the buffer fluid so that the buffer fluid contacts the sample. In yet another embodiment of the present invention, the sample collector has a pump which draws the sample into the sample collector.

This invention also relates to a sample testing device that includes a buffer container which can contain buffer fluid, the buffer container having a weakened portion, a filter having a securement for holding a test strip, the test strip, an end of which is held by the securement, and a test strip container having a receptacle dimensioned and disposed to accommodate the filter, so that when the filter is accommodated by the test strip container, the test strip is disposed in the receptacle. The invention also includes a sample collector for holding a sample therein and which is shaped to receive the buffer container, the sample collector having a channeling member. When the buffer container is squeezed, the weakened portion fails and the buffer fluid in the buffer chamber contacts the sample and passes through the lumen of the channeling member to the filter. As the buffer fluid flows through the lumen of the sample collector the buffer fluid that has contacted the sample passes through the filter to the test strip.

This invention also provides a sample testing device that includes a buffer container which can contain buffer fluid therein, a filter having a securement for holding a test strip, the test strip, an end of which is held by the securement, a test strip container having a receptacle dimensioned and disposed to accommodate the filter, so that when the filter is held therein the test strip is disposed in the receptacle, and a sample collector including a pump for holding the sample.

Another aspect of this invention is a method for testing a sample. This is done by obtaining the sample, placing the sample in a sample collector, positioning a buffer container having buffer fluid therein above the sample collector, positioning the sample container above a filter, the filter having a test strip in contact therewith, and causing the buffer fluid to flow downward from the buffer container over the sample and through the filter to the test strip.

BRIEF DESCRIPTION OF THE DRAWINGS

The accompanying drawing figures are illustrative, and like reference characters denote similar elements throughout the several views.

DETAILED DESCRIPTION OF THE PREFERRED EMBODIMENT

As depicted in the accompanying drawings, the present invention is directed to a compact, self-contained testing device which can be used to obtain and analyze fluid samples, and more particularly, samples of bodily fluid. By way of non-limiting example, the sample testing device can include an elongate body portion which accommodates a strip of test material, a filter that holds the test material, and a buffer container holding material which first reacts with the sample and then which reacts with the test strip to indicate the results of the test. A sample collector serves to combine the material in the buffer container with the sample and which then guides that mixture to the filter.

Construction of the Sample Testing Device

Figure 1:
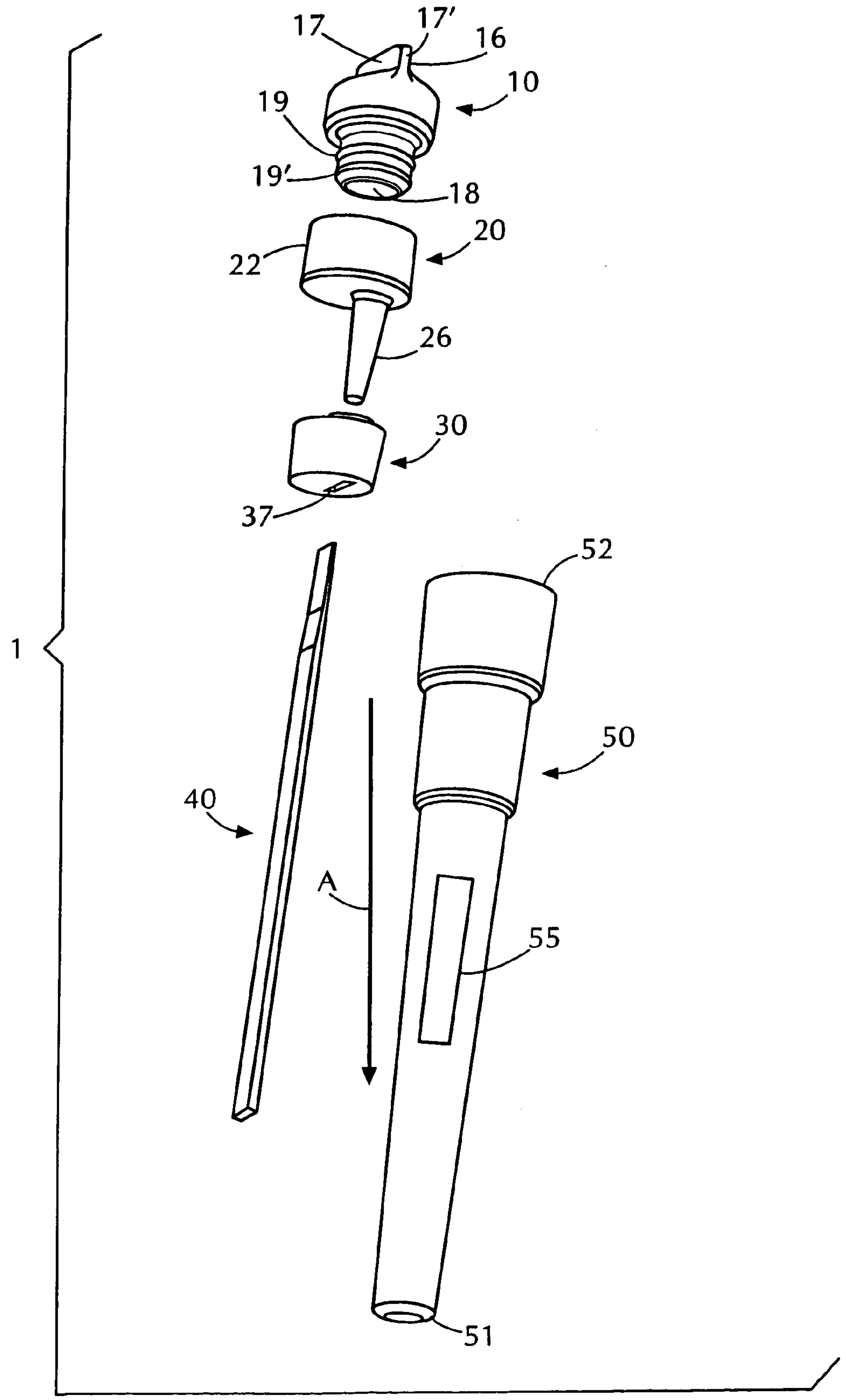
FIG. 1 is an exploded perspective view of a sample testing device in accordance with this invention.
Figure 2:
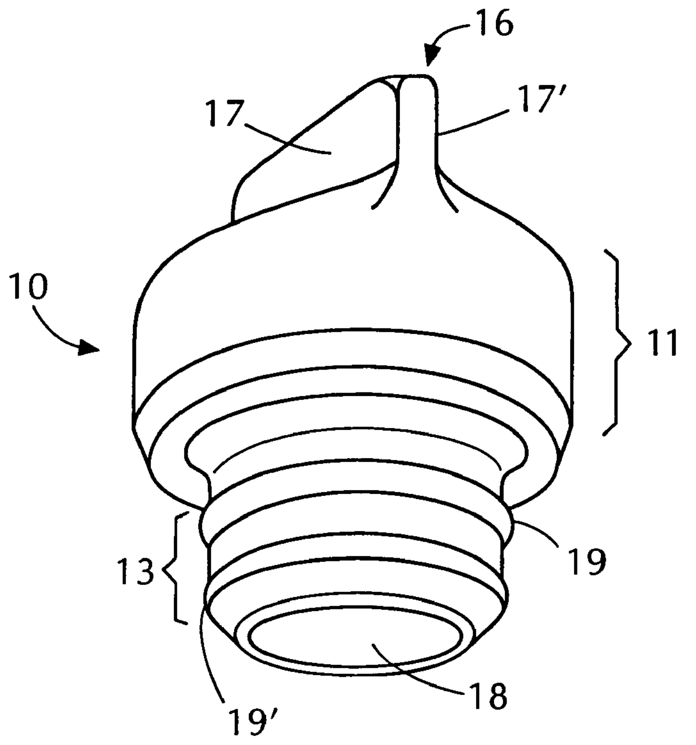
FIG. 2 is a perspective view showing the front and a portion of the perimeter of a buffer container which can be used with the present invention.
Figure 3:
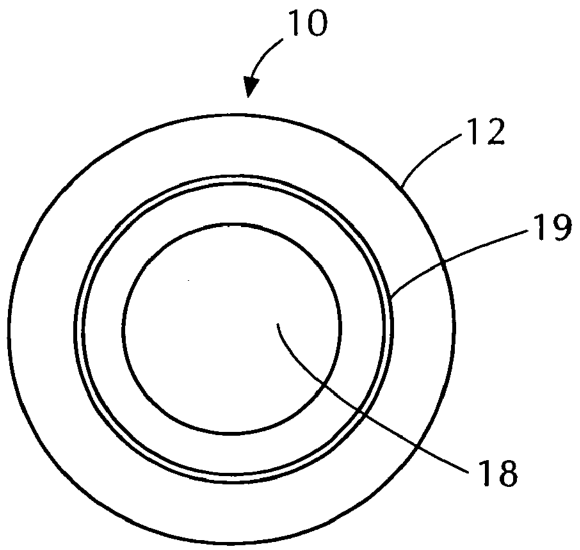
FIG. 3 is a bottom plan view of the buffer container depicted in FIG. 2.
Figure 4A:
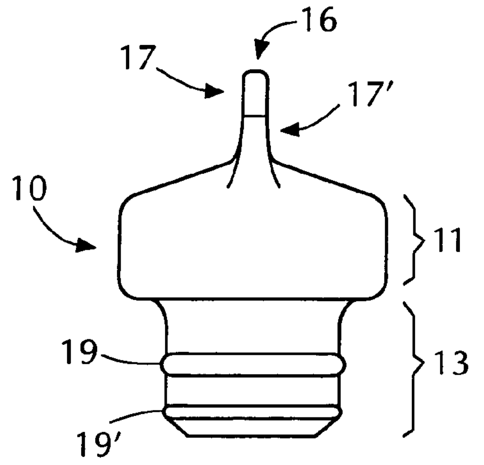
FIG. 4A is a side elevational view of the buffer container depicted in FIG. 2.
Figure 4B:
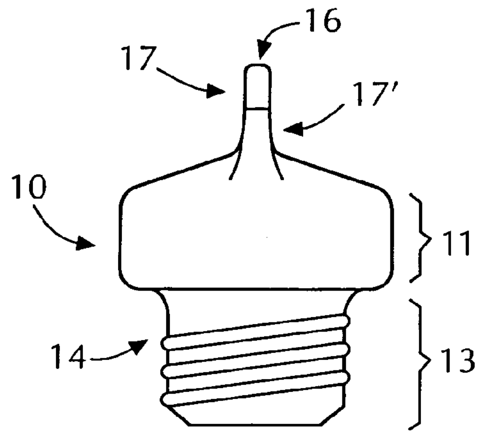
FIG. 4B is a side elevational view of an alternate buffer container
Figure 5:
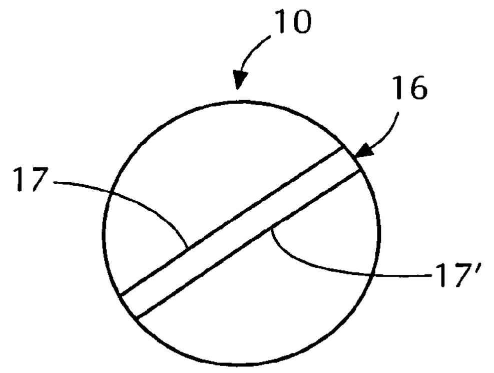
FIG. 5 is a top plain view of the buffer container depicted in FIG. 2.

FIG. 1 depicts in exploded form a sample testing device 1 according to a first embodiment of the present invention.

Sample device 1 includes a buffer container 10, a sample collector 20, filter 30, test strip 40 and test strip container 50. Each of these components will be discussed in turn.

As shown in FIGS. 2-5, buffer container 10 is a plug-shaped, generally-cylindrical, member having a top portion 11, a base portion 12, a body portion 13, and a pierceable membrane 18. The buffer container 10 is hollow and, when loaded into the sample device for testing, contains a buffer fluid (not shown).

By way of non-limiting example, the top portion 11 of the buffer container 10 is preferably contoured, with a ridge-shaped grip 16 having side walls 17 and 17'. The benefits of this arrangement will be discussed hereafter.

In one embodiment of the present invention, buffer container 10 and sample collector 20 are initially held in place by a press and snap detent (19). A second press and snap detent (19') holds and seals buffer container 10 in firm contact with sample collector 20 when buffer container 10 is pressed downward onto piercing edge 24 of piercing member 23, thereby puncturing pierceable membrane 18 and releasing the buffer fluid housed in buffer container 10. See FIG. 4A.

In an alternative embodiment of the present invention, the body portion 13 of buffer container 10 has a threaded outer surface 14 which is arranged to engage matching threads formed on the inner surface 21 of the sample collector 20. This way, the buffer container 10 can be joined to the sample container 20 in fluid-tight fashion. See FIG. 4B. Other schemes for obtaining a fluid-tight connection, such as forming elastic projections (not shown) on or applying one or more O-rings to the body portion 13 also could be employed. Alternatively, a fluid-tight press fit between flat surfaces also could be used.

Preferably, the outer diameter of sample collector 20 and the inner diameter of buffer container 10 are sized so that, when joined, sample collector 20 and buffer container 10 frictionally engage one another.

Other shapes and arrangements of elements for joining buffer container 10 and sample collector 20 are also suitable, provided such elements allow for fluid communication from buffer container 10 to sample collector 20.

Pierceable membrane 18 of buffer container 10 forms a frangible, fluid impermeable barrier for retaining buffer fluid in the buffer container 10. Pierceable membrane 18 may be formed of any non-reactive material which is capable of containing the buffer fluid in buffer container 10 and which can be pierced by the piercing edge 24 of the piercing member 23 formed in the sample collector 20. Examples of materials suitable for forming pierceable membrane 18 include, but are not limited to, metal foil, polymeric membrane, glass, or plastic. Also, the pierceable membrane 18 could be formed with a suitably sized and shaped score or pre-stressed area (not shown) which will rupture when contacted by the piercing edge 24.

Figure 6:
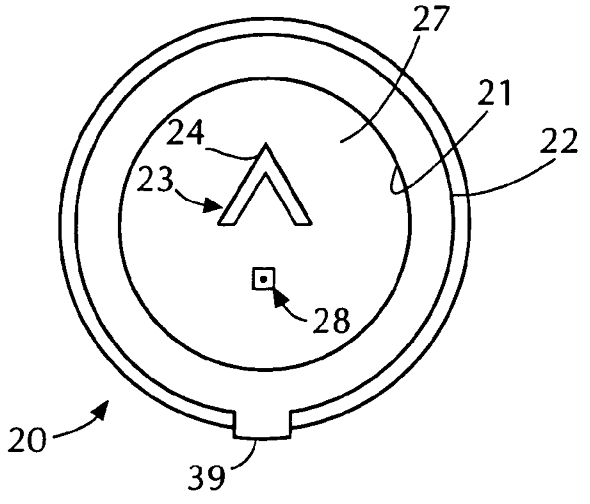
FIG. 6 is a top plain view of a sample collector which can be used with the present invention.
Figure 7:
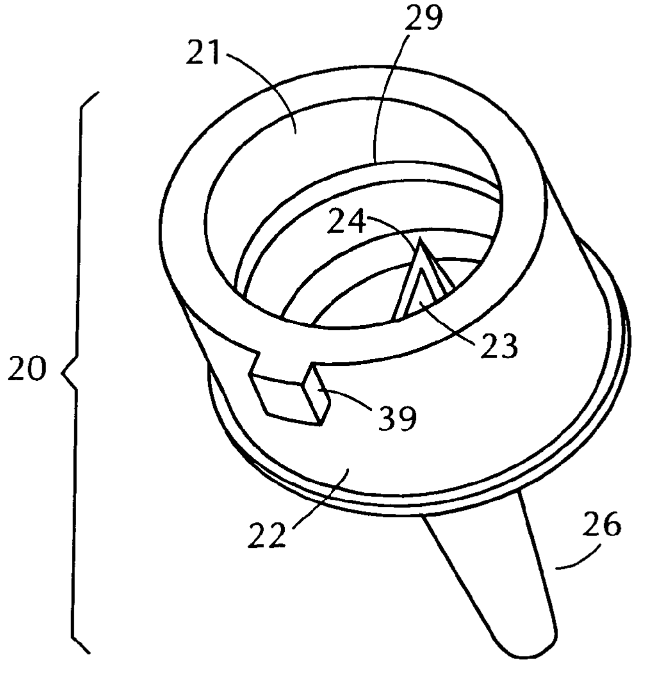
FIG. 7 is a perspective view showing the top and a portion of the perimeter of the sample collector depicted in FIG. 6.

With reference now to FIGS. 6 and 7, sample collector 20 includes an inner surface 21, an outer surface 22, and an interior base 27. The sample collector 20 also includes piercing member 23. The upper edge of piercing member 23 includes a sharp piercing edge 24 that contacts and pierces pierceable membrane 18 of buffer container 10 when the buffer container 10 is joined to the sample collector, thereby releasing the buffer fluid (not shown). Piercing member 23 could be shaped to facilitate the flow of buffer fluid.

With continued reference to FIGS. 6 and 7, sample collector 20 also includes an elongate and hollow channeling member 26. The lumen 28 runs from the tip of the channeling member 26 to the base 27 of the sample collector, for reasons explained hereafter.

Turning now to FIGS. 8-11, filter 30 and test strip 40 will be described.

Filter 30 serves several purposes. It secures the test strip, absorbs and contains buffer solution and sample, and provides a controlled fluid flow to the test strip, and filters impurities from the material being tested. By way of non-limiting example, if the material being tested is blood, it may be desirable to separate out the red and white blood cells and platelets from the blood plasma that is to be tested.

The filter 30 can be made from a wide variety of materials, provided such materials are non-reactive and serve flow controlling and filtering functions. By way of non-limiting example, the filter can be made from ceramic or glass frit. By carefully selecting the size of the flit particles, and the manner in which those particles are processed to form filter 30, filter porosity can be carefully regulated to insure the proper rate of fluid flow, fluid absorption or rate of fluid, and that the proper components are separated from the sample being tested. Also by way of non-limiting example, other materials such as textiles, whether woven or non-woven, metal, polymer or other mesh, or perforated membranes could be used alone, in combination, or in conjunction with other materials to provide the flow controlling and filtering functions. In addition, the filter can be coated with various flow-enhancing compounds such as detergents, surfactants and viscosity agents to alter the flow property of liquids therethrough.

Figure 11:
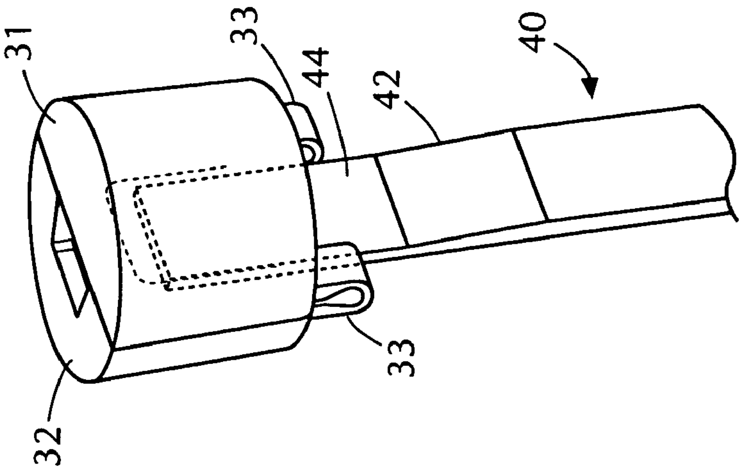
FIG. 11 is a front perspective view showing the test strip securement and test strip after the test strip has been secured.

In addition to flow control and filtering impurities from the test sample, filter 30 holds the test strip 40 in place in the chamber 56 of the test strip container 50, as depicted in FIG. 11. When test strip 40 is in prescribed contact with filter 30, good consistent fluid transfer is possible.

One way that this can be done is by providing a filter 30 having two portions which, when brought together, have a plug shape and which are arranged to hold the test strip 40 between them. Thus, the filter 30 includes a securement for the test strip 40.

Figure 8:
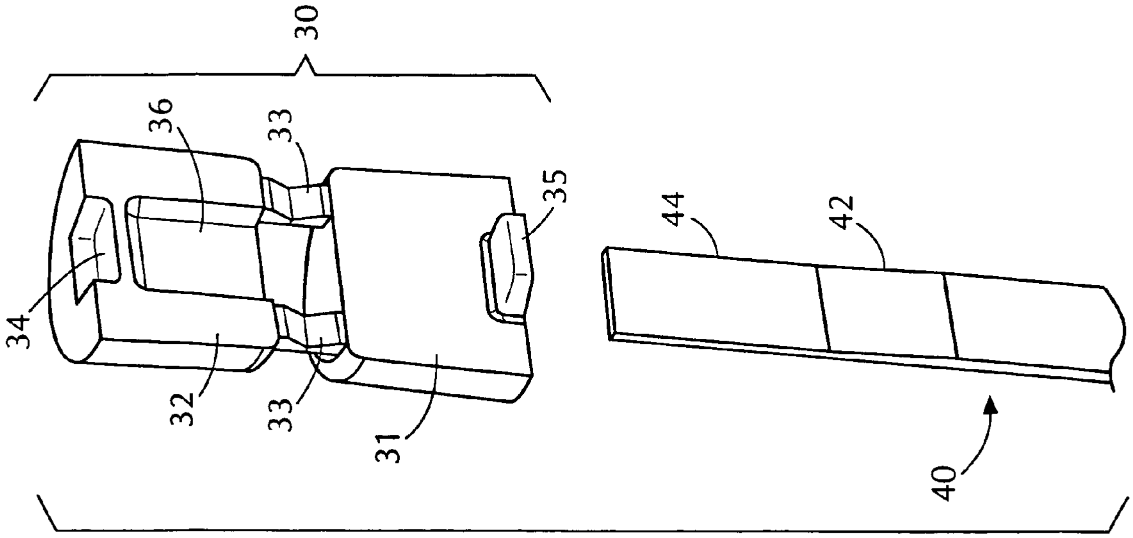
FIG. 8 is a front perspective view showing a preferred embodiment of the test strip securement and test strip.
Figure 10:
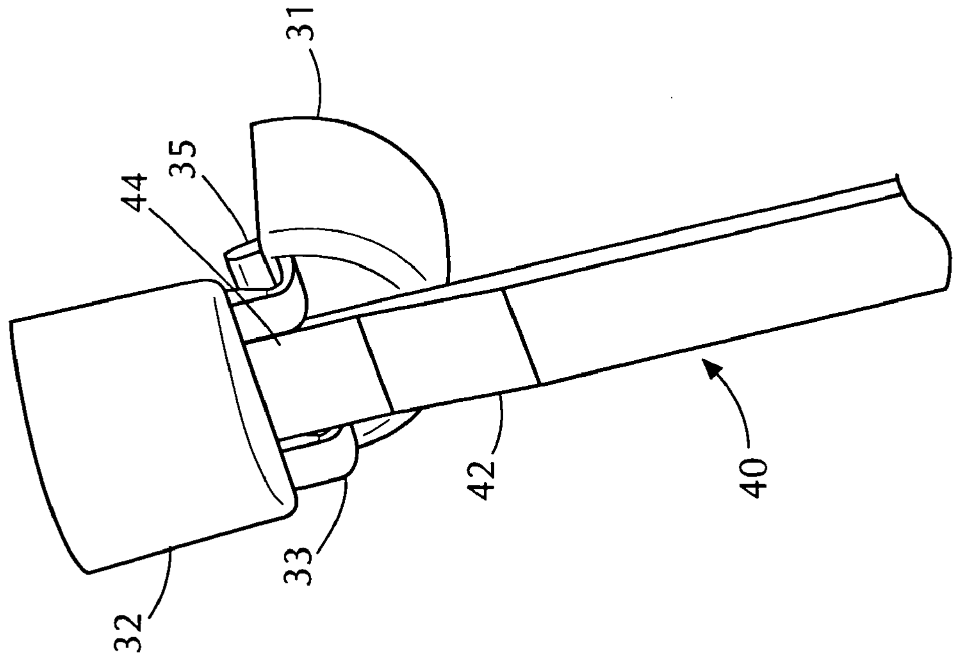
FIG. 10 is a rear perspective view showing engagement of the test strip securement and test strip depicted in FIG. 8.

As depicted in FIG. 8, filter 30 includes a flat portion 31 and a notched portion 32, having a notch 36, which are joined together by living hinges 33. Living hinges 33 allow the flat and notched portions 31, 32 of the filter 30 to be brought together, as shown in FIGS. 10 and 11.

If desired, living hinges 33 can be replaced with any other suitable structure for joining the flat and notched portions 31, 32. Alternatively, the flat and notched portions need not be joined, but could still be held together when inserted in the portion 57 of the test strip container 50 shaped to hold the filter 30.

Figure 9:
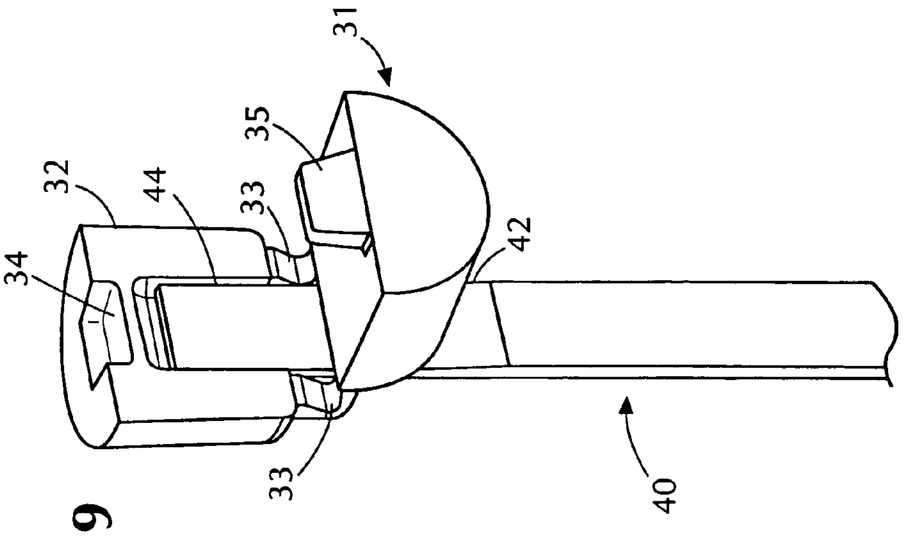
FIG. 9 is a front perspective view showing partial engagement of the test strip securement and test strip depicted in FIG. 8.

With reference now to FIGS. 8 and 9, notch 36 is preferably shaped to receive securely the end 44 of test strip 40. By making notch 36 somewhat less deep than the thickness of the end 44 of the test strip 50, the end 44 will be securely captured between the flat and notched portions 31, 32 of the assembled filter 30. Notch 36 also facilitates the secure capture of the end 44 of the test strip 40 between the flat and notched portions 31, 32 of the filter 30 without undue deformation of the filter.

Once the flat and notched portions 31, 32 of filter 30 have been brought together, capturing the end 44 of the test strip 40 therebetween, as shown in FIG. 11, they must be secured together. To hold the flat and notched portions 31, 32 of filter 30 together, the flat portion 31 can be provided with a protruding key 35, and flat portion 32 can be provided with a matching recess 34. When the key 35 and recess 34 are properly shaped, the key 35 being slightly wider than the recess 34, they will hold the flat and notched portions 31, 32 together by way of an interference fit, securing the test strip 40 in place. Alternatively, a reverse taper (not shown) could be used, in which case the key 35 could be bent upward slightly as the flat and notched portions 31, 32 are brought together, and then when in registry with the recess 34, the key 35 could be bent downward into the recess 34. Also by way of non-limiting alternative, the key and recess could be welded or adhered together, joined by fasteners, or secured together by any other suitable technique, without departing from the scope of the present invention.

Also by way of non-limiting example, filter 30 could be provided as a single, approximately cylindrical member (not shown) having a slot therein corresponding generally in position to notch 36. By making that slot somewhat smaller than notch 36, the end 44 of test strip 40 could be held in place by a simple press fit. That is, the end 44 of test strip 40 could be urged into place in the slot using one or more thin, stiff blades to position the end 44 in the slot.

Test strip container 50 will now be described with reference to FIGS. 1 and 12.

The test strip container 50 serves several different functions. First, it holds all of the other components of the sample testing device 1. Second, during use the test strip container 50 holds the sample and buffer fluid as they mix and are drawn into test strip 40. Third, the test strip container isolates the sample and buffer fluid from the environment.

Figure 12:
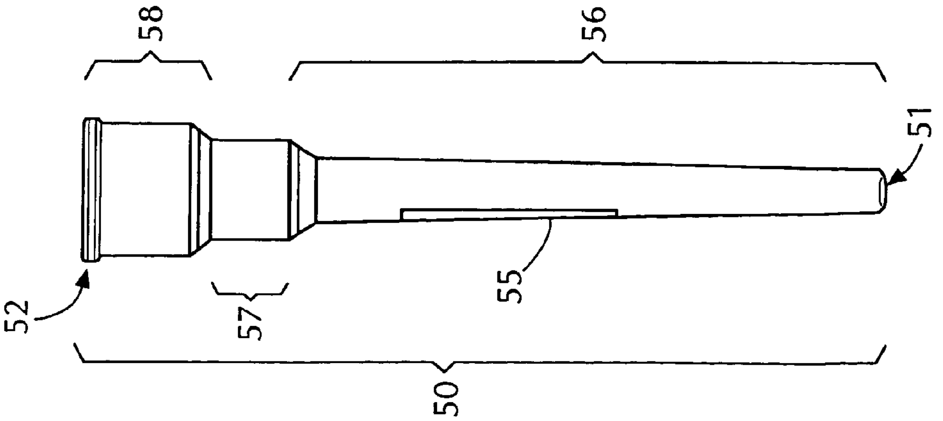
FIG. 12 is a side elevational view of a test container which can be used with the present invention.

With continued reference to FIGS. 1 and 12, test strip container 50 is preferably a generally cylindrical container closed at its bottom end 51 and open at its open end 52 to enable loading with all of the components of the sample testing device 1. Since test strip container 50 holds the buffer container 10, sample collector 20, filter 30 and test strip 40, the profile of the test strip container 50, seen from the side as in FIG. 12, can be stepped. This way, each stepped region is approximately the same size as the part of the sample testing device 1 which it contains. The longest and narrowest part of the test strip container 50 is the chamber 56, which corresponds to the test strip 40. Portion 57 of the test strip container 50 corresponds to and holds filter 30 and is somewhat wider than the chamber 56. Portion 58 of the test strip container 50 is in turn somewhat wider than the portion 57, and corresponds to and holds the buffer container 10.

As shown in FIG. 12, test strip container 50 is closed at bottom end 51 and open at end 52. Test strip container 50 is sized at position 57 to accommodate filter 30 and test strip 40 which is secured to filter 30. Filter 30 fits within test strip container 50 without contacting the exposed portion of test strip 40 directly. Test strip container 50 is dimensioned at position 58 to securely hold sample collector 20 and buffer container 10 by a friction fit. By way of non-limiting example, the buffer container 10 and sample collector 20 could be welded or bonded into place. Also, buffer container 10 can be joined to sample collector 20 before sample collector 20 and buffer container 10 are inserted into test strip container 50.

As shown in FIG. 1, test strip 40 can itself be a test strip such as are known. Such test strips are customarily treated with a reagent compatible with the test being performed.

If, as is preferred, the test strip 40 is a visual test strip, meaning the results of the test are determined by observing a visual indication on the test strip, the test strip container 50 should be constructed so that the test strip 40 can be viewed. This can be done by forming the entire test strip container 50 from transparent material such as glass or plastic. Alternatively, opaque or non-transparent material could be used and at least one transparent window 55 could be formed in the chamber 56 of the test strip container 55 so that test strip 40 can be viewed therethrough.

Test strip container 50 can be made from any suitable nonreactive material, such as glass, plastic or ceramic, or a combination thereof. The test strip container 50 can be formed using any known technique. Injection molding of glass or plastic is presently thought to be preferable.

Sample testing device 1 is preferably packaged in sterile fashion with all, or at least some, of its components, buffer container 10, sample collector 20, filter 30, test strip 40 and test strip container 50 assembled together. It will be appreciated that because the sample collector 20 includes a piercing member 23 designed to pierce the membrane 18 of buffer container 10 and allow the buffer fluid therein to run out, a protective piece such as a flat disc of material that must be removed before use can be provided between the sample collector 20 and the buffer container 10. This way, the membrane 18 will not be ruptured inadvertently. Alternatively, those components could be packaged in unassembled form for later assembly by the user. Sterilization could be and packaging could be accomplished using any suitable technique now known or hereafter developed.

Although it is presently thought to be preferable to provide the buffer container 10 of the sample testing device 1 loaded with the buffer fluid, the buffer container 10 could be provided empty for filling with buffer fluid by the user. In such an arrangement, the buffer container 10 could be made entirely or just in part from a self-sealing material. To fill the buffer container 10, the user could take a hypodermic syringe containing a sufficient amount of the buffer fluid, and drive the syringe needle through the self-sealing material. Once the needle is inside the buffer container 10, the user would inject the buffer fluid into the buffer container and withdraw the needle therefrom. The self-sealing material then closes the opening made by the needle, retaining the buffer fluid inside the buffer container.

An alternate embodiment of the present invention will now be described with reference to FIGS. 13-15.

Figure 15:
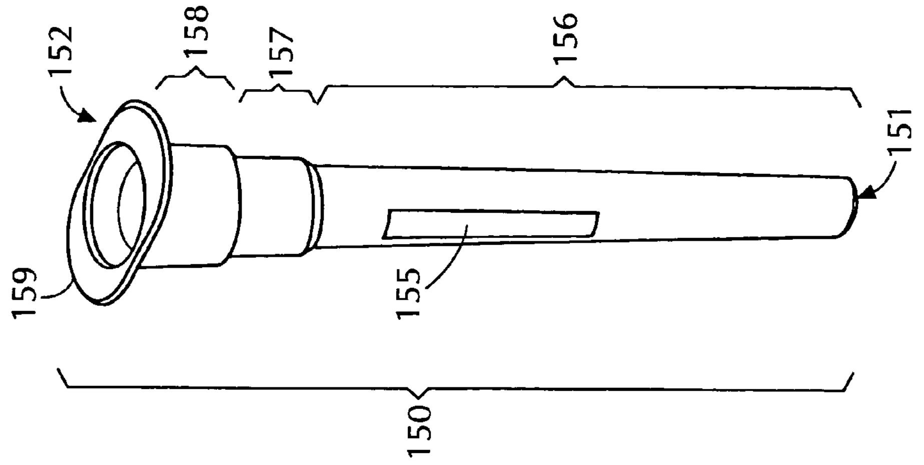
FIG. 15 is a side elevational view of the test container depicted in FIG. 13.
Figure 14:
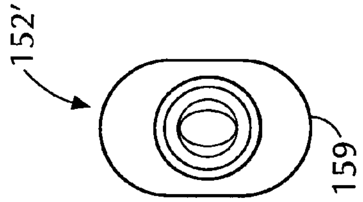
FIG. 14 is a top plan view of the test strip container depicted in FIG. 13.
Figure 13:
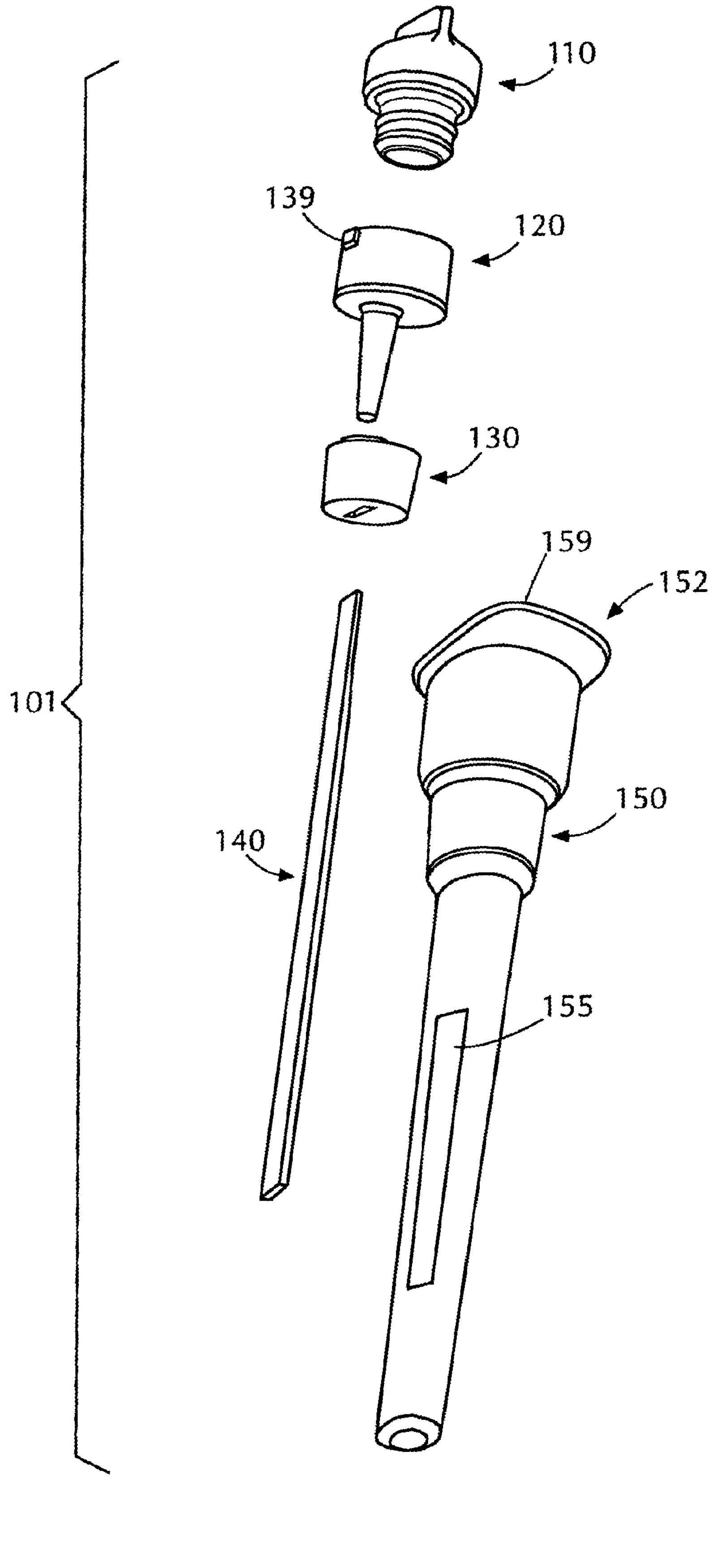
FIG. 13 is an exploded perspective view of another embodiment of a sample testing device in accordance with this invention.

As depicted in FIGS. 13-15, the open end 152 of test strip container 150 has been modified to included a flange 159 extending outward in a plane generally perpendicular to the long axis of the test strip container 150. By way of non-limiting example, flange 159 can be oval, as depicted, or round (not shown). Flange 159 helps the person using the sample testing device 101 grasp the test strip container 150. Flange 159 also prevents test strip container 150 from rolling and provides a flat surface on the back of test strip container 150 for marking or writing.

Figure 16:
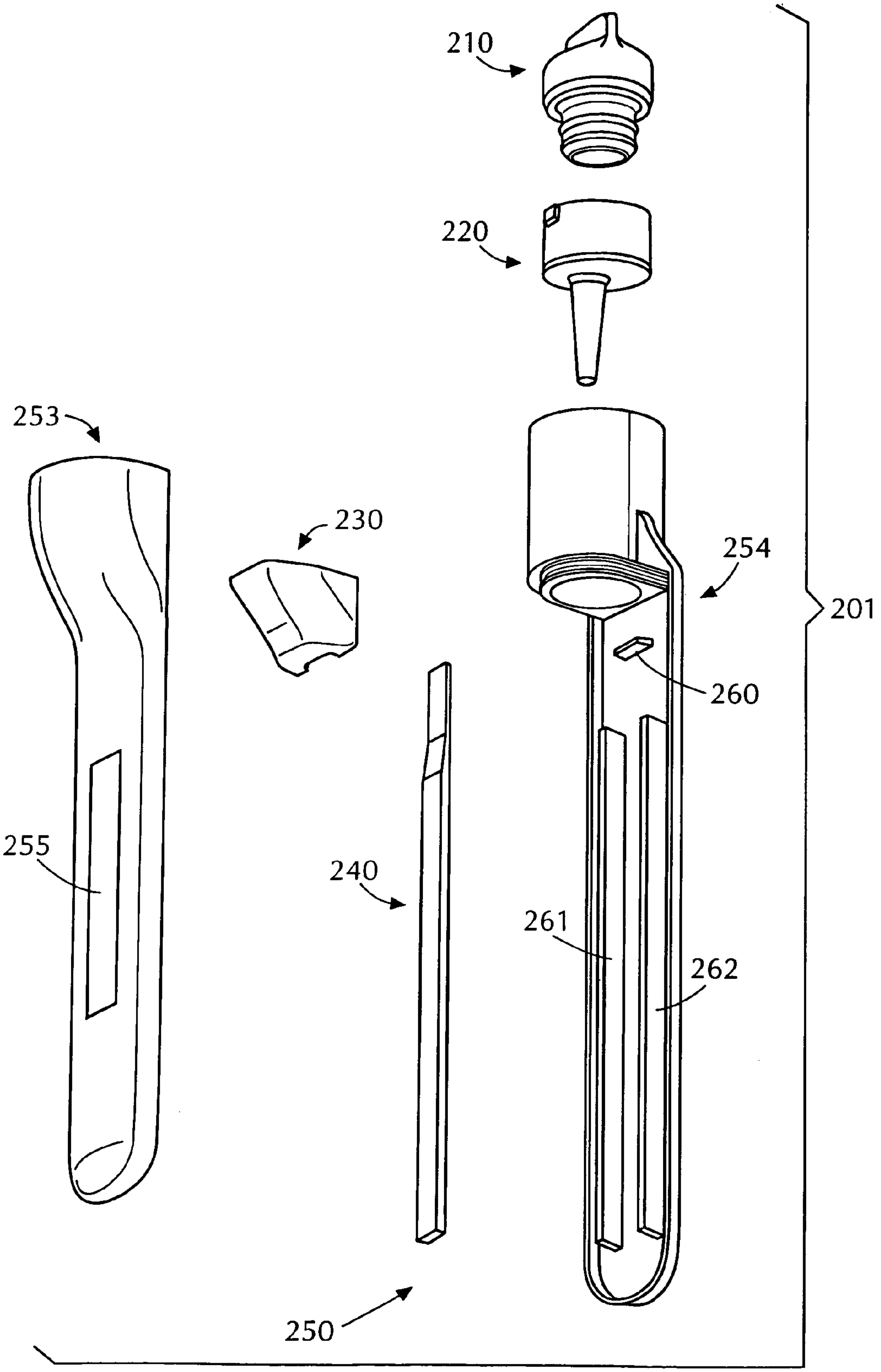
FIG. 16 is an exploded perspective view of still another embodiment of a sample testing device constructed in accordance with the present invention.

Another alternate embodiment of a sample testing device 201 as claimed is depicted in FIG. 16. Whereas the previous embodiments employed a unitary test strip container 50, 150, this embodiment provides a multi-piece test strip container 250 having a cover 253 and a body 254 which fit together and hold the other components. Cover 253 can have a generally flat spatulate region corresponding to and accommodating the position of test strip 240, which flares out into a more open region corresponding to the sample collector 220 and the buffer container 210. This shape allows for a more compact and easier to handle design.

As depicted in FIG. 16, the body 254 can have a pair of projections 261 and 262 which are dimensioned and disposed so as to be overlapped by test strip 240. This way, test strip 240 is kept from undue contact with the rest of the body 254. Test strip 240 is itself secured between filter 230 and projection 260. Filter 230 is preferably shaped to conform to the adjacent portion of the cover 253. This way, when the cover 253 is joined to the base 254, the filter is urged against the base 254, thereby capturing the test strip 240 between the filter 230 and the projection 260.

Cover 253 can be transparent, allowing observation of the test strip 240, or opaque, in which case a window 255 for viewing the test strip 240 can be provided.

The cover 253 and base 254 can be molded or machined to shape from any suitable clinically-inert, non-porous and rigid material. By way of non-limiting example, polyethylene and polypropylene are clinically inert plastics.

They can be joined using any suitable techniques now known or hereafter developed. By way of non-limiting example, the cover 253 and base 254 could be snapped together, ultrasonically bonded or adhered.

The sample container 220 and buffer container 210 can be constructed in the manner already described.

Figure 18:
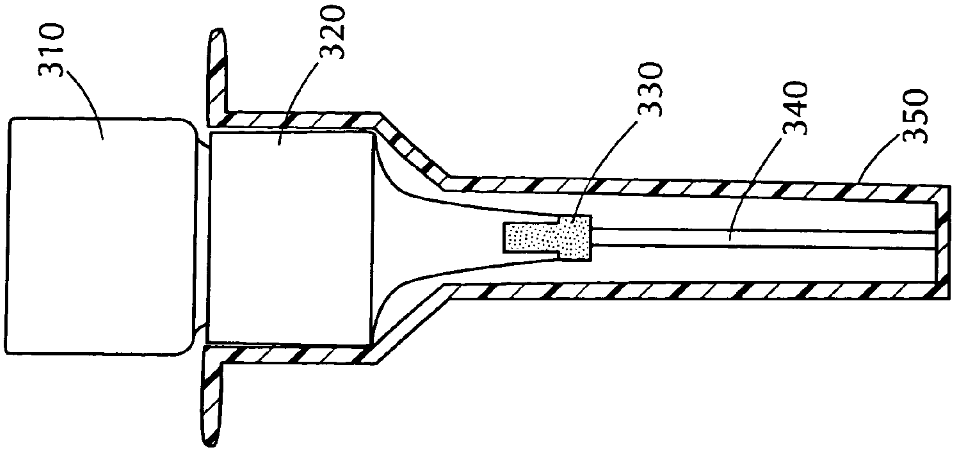
FIG. 18 is a front elevational view showing a cross-section of a further embodiment of a sample testing device constructed in accordance with the present invention.
Figure 17:
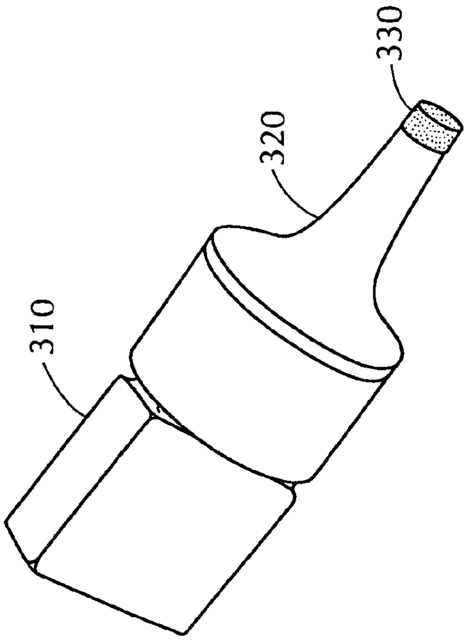
FIG. 17 is a perspective view showing the front, one side and top of yet another embodiment of a buffer container, sample collector and filter that can be used in accordance with the present invention.
Figure 19:
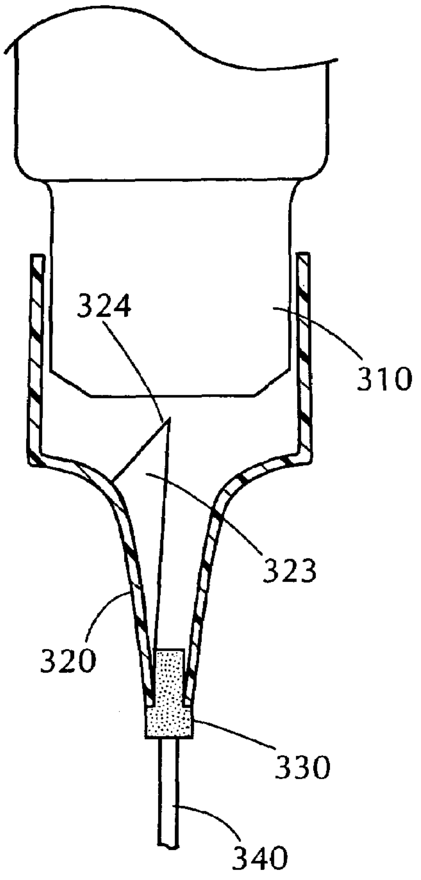
FIG. 19 is a side elevational view showing a cross-section of a buffer container, sample collector and filter that can be used in accordance with the present invention as shown in FIG. 18.

Another embodiment of the sample testing device is depicted in FIGS. 17-19. FIG. 17 illustrates the relationship between buffer container 310, sample collector 320 and filter 330. FIG. 18 illustrates a sample testing device including buffer container 310, sample collector 320, filter 330, test strip 340 and test strip container 350. As illustrated therein, filter 330 fits into a suitably-dimensioned portion of sample collector 320. A friction fit between the sample collector 320 and the filter 330 ensures that only liquid that has passed through filter 330 contacts test strip 340. Alternatively, any other suitable sealing arrangement, such as O-rings, could be used.

As shown in FIG. 19, piercing member 323 with piercing edge 324 punctures the bottom of buffer container 310 thereby releasing the buffer fluid contained therein. The buffer fluid then interacts with the sample housed in sample collector 320.

Filter 330 is introduced into the bottom opening of sample collector 320 and forms a fluid-tight seal therewith. The sample is then introduced via the top opening of sample collector 320, if necessary, using a pipette or dropper. In an embodiment of the present invention, sample collector 320 is contoured to allow for sputum to be easily collected. Filter 330 seals the bottom opening of sample collector 320, thereby preventing the sample from exiting through the bottom of sample collector 320.

Buffer container 310 is introduced into the top opening of sample collector 320. Piercing edge 324 of piercing member 323 pierces buffer container 310, thereby releasing the buffer fluid contained therein. The buffer fluid mixes with sample in sample collector 320 and the resulting mixture passes through filter 330 and contacts test strip 340. In this embodiment, filter 330 serves several functions. Filter 330 seals the bottom opening of sample collector 320 thereby preventing the sample from escaping, absorbs and contains buffer solution and sample, provides a controlled fluid flow to test strip 340, and filters impurities from the material being tested.

Figure 20A:
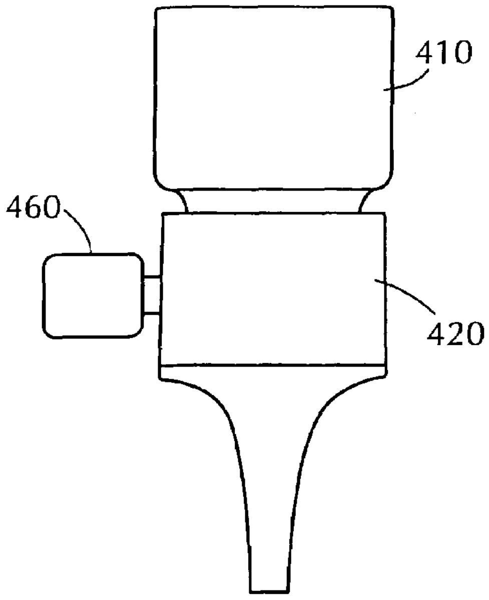
FIG. 20A is a front elevational view of an alternative buffer container and sample collector that can be used in accordance with the present invention.
Figure 20B:
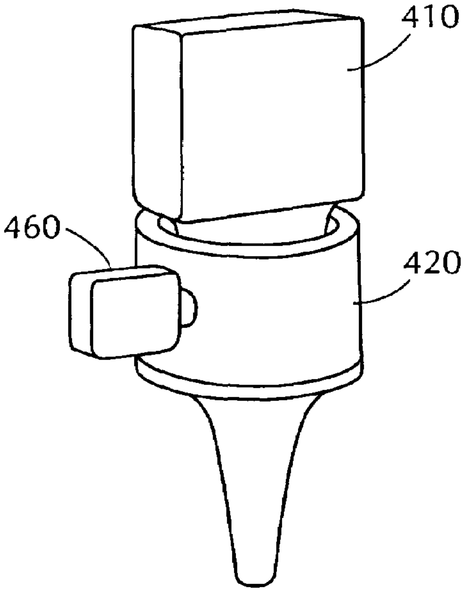
FIG. 20B is a perspective view showing the front, one side and top of an alternative buffer container and sample collector that can be used in accordance with the present invention.

A further embodiment of the present invention is depicted in FIGS. 20A-23. FIGS. 20A and 20B illustrate the interaction among buffer container 410, sample collector 420 and pump 460. Pump 460 is preferably made of an elastic or polymeric material which is capable of being compressed by squeezing so as to expel air therefrom. Releasing the pump 460 then draws air or other fluid toward the pump.

Figure 21:
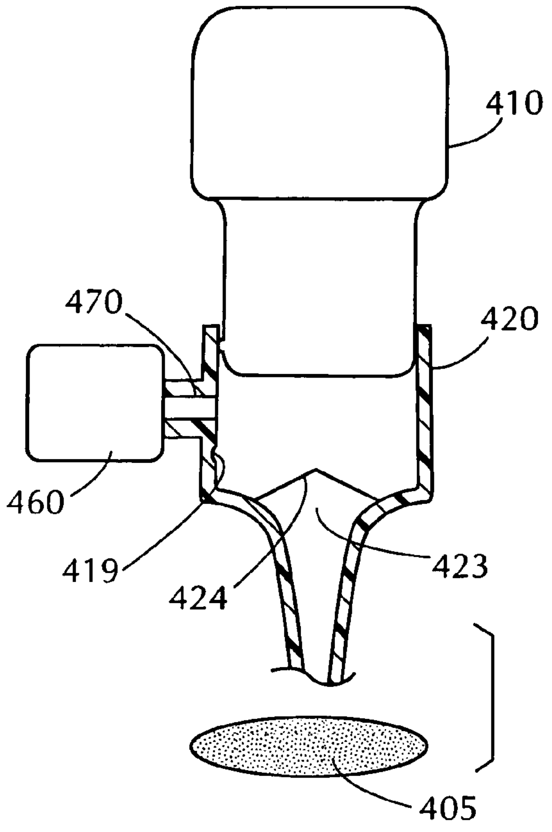
FIG. 21 is a front elevational view in cross-section of an alternative buffer container and sample collector that can be used in accordance with the present invention.

As shown in FIG. 21, a portion of sample 405 is drawn into sample collector 420 when compressed pump 460 is released thereby creating a vacuum in sample collector 420. Sample 405 flows into sample collector 420 to fill the vacuum created by the release of pump 460. After sample 405 is drawn into sample collector 420, sample collector 420 is placed inside test container 450 atop filter 430. Filter 430 has a fluid-tight fit with test container 450 thereby ensuring that any liquid which contacts test strip 440 has first passed through filter 430.

Buffer container 410 is then inserted into sample collector 420. Buffer container 410 fits securely into sample collector 420 and seals air passage 470 thereby inhibiting the operation of pump 460. Sample collector 420 has at least one piercing edge 424 on a piercing member 423. Piercing edge 424 pierces buffer container 410 thereby releasing the buffer fluid contained therein. The buffer fluid mixes with sample 405 and the resulting mixture contacts filter 430.

Buffer container 410 can be held in place in sample collector 420 by a press and snap detent 419. A comparable second press and snap detent (not shown) secures buffer container 410 in firm contact with sample collector 420 once buffer container 410 is pressed downward onto piercing edge 424 of piercing member 423, thereby puncturing the pierceable membrane (not shown) and releasing the buffer fluid housed in buffer container 410. See FIG. 21. The detent can provide a fluid-tight seal between the buffer container 410 and the sample collector 420. Again, any other known or discovered sealing can be used.

Figure 22:
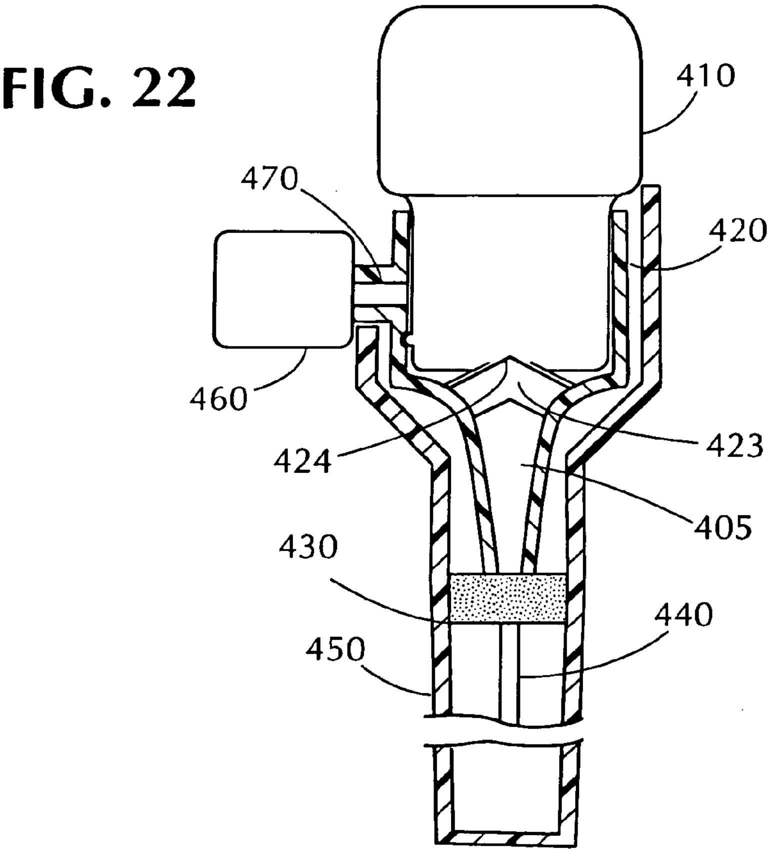
FIG. 22 is a front elevational view in cross-section of a further embodiment of a sample testing device constructed in accordance with the present invention.

FIG. 22 depicts the sample collector 420, buffer container 410, pump 460 and air passage 470 integrated with filter 430, test strip 440 and test container 450. Buffer fluid contacts the sample 405 contained in sample collector 420 as discussed above. The resultant mixture including the buffer fluid and sample 405 contacts filter 430. Filter 430 contacts test strip 440 which is housed in test strip container 450.

Figure 23:
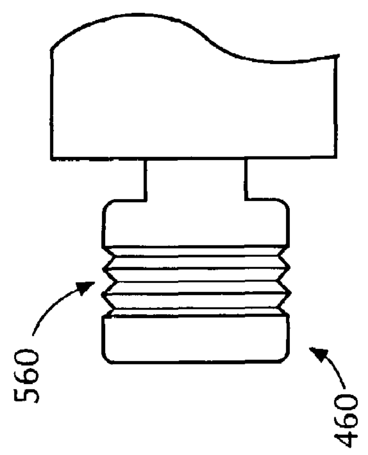
FIG. 23 is a side elevational view of an alternative pumping mechanism.

FIG. 23 depicts an alternate embodiment of pump 460 wherein the pump 460 is accordion-shaped 560.

Figure 24:
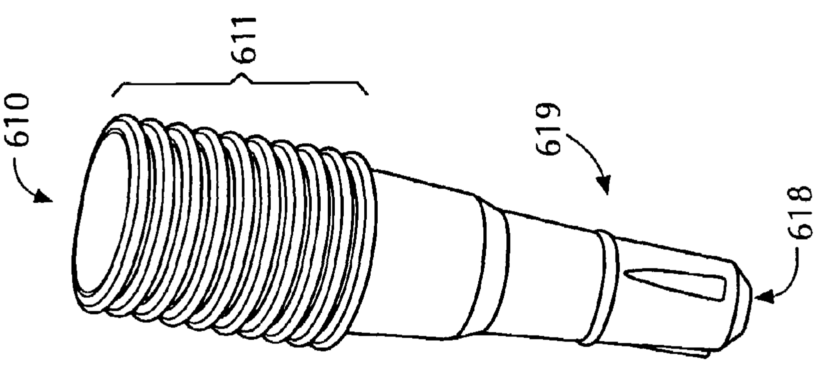
FIG. 24 is a perspective view showing the front and top of a cylindrical buffer container that may be used with the present invention.

FIG. 24 depicts an alternate buffer container 10 wherein the buffer container 610 has a bellowed top portion 611 in order to facilitate expulsion of the buffer solution from the buffer container 610 into the sample collector (not shown). Buffer container 610 is initially secured to the sample collector by the interaction of raised ring 619 with a matching groove (not shown) formed in the sample collector (not shown). The sample collector can include a second depression (not shown) which holds and seals buffer container 610 in firm contact with the sample collector when the buffer container 610 is pressed downward onto the piercing edge of the piercing member, thereby puncturing a pierceable membrane 618 of the buffer container 610 and releasing the buffer fluid housed in buffer container 610.

By pressing downward and compressing the bellows region 611 of buffer container 610, pierceable membrane 618 of buffer container 610 is pierced by the piercing edge (not shown) of the piercing member (not shown). Liquid in the buffer container 610 then flows out of buffer container 610 and into the sample collector (not shown) under the influence of gravity. In a further embodiment, pierceable membrane 618 of buffer collector 610 can have a weakened portion (not shown) where it will fail when stressed by the raised pressure of the liquid inside the compressed bellows 611.

Figure 25:
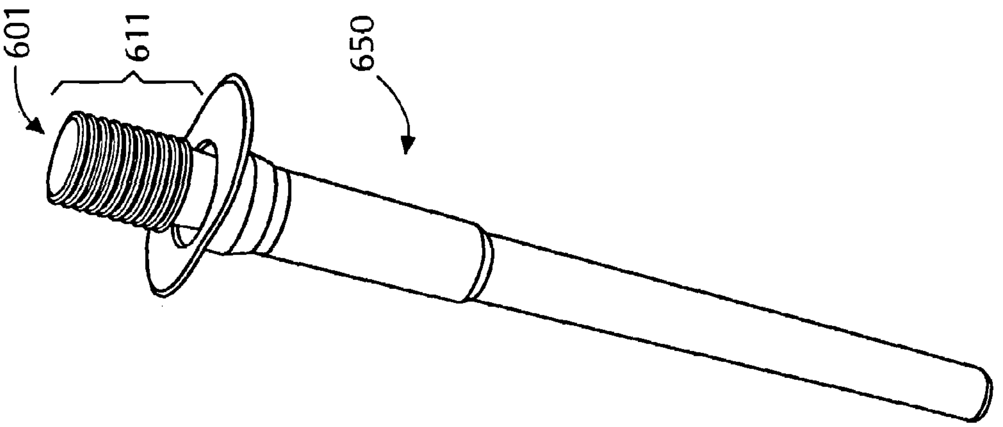
FIG. 25 is a perspective view depicting the alternative buffer container of FIG. 24 used with the sample testing device of FIG. 13.

FIG. 25 illustrates buffer container 610 loaded into a sample testing device 601 comparable to that depicted in FIGS. 13-15. Buffer container 610 is tapered so that bellows 611 of buffer container 610 does not fit in the open end of test strip container 650.

It should be understood that while various components described above have been shown as being circular in cross-section, this geometry is merely preferable, and not required. Other shaped components also could be used without departing from the present invention.

Use of the Sample Testing Device

The present invention functions by mixing a test sample with a buffer fluid, filtering the mixture, and then absorbing the mixture using a piece of reactive test material. A reactive test material is a material which changes one or more properties when in the presence of a specific substance. Here, the properties which change are preferably visual. By way of non-limiting example, the test strip can change color or develop one or more lines, bands, dots or patterns when certain materials are applied thereto. The precise manner in which this is accomplished will be discussed.

Once sample testing device 1 has been removed from its packaging it can be prepared for use as follows.

A sample of material (not shown) to be tested is introduced into the sample collector 20. Examples of fluids which may be used as samples in the testing system of the present invention include, but are not limited to, saliva, cerebrospinal fluid, serum, whole blood, plasma, vaginal fluid, semen, and urine. These bodily fluids may be obtained from either humans or animals. In addition, fluids obtained from plants, trees, soil, the environment and other sources may be used as samples. Depending upon the nature of the sample, the sample can be loaded into the sample collector 20 in any of several ways.

If the liquid is not overly viscous, it can be drawn upward into the lumen 28 of the channeling member 26 through capillary action. By way of example, the tip of the channeling member 26 can be dipped into a patient's blood, where it will be drawn up into the lumen 28. In some cases, the patient may be bleeding freely, for example, if the patient has a cut or open wound. Alternatively, it may be necessary or preferred to draw blood from the patient. This can be done by jabbing the patient, say, in a finger, toe or earlobe, with a sharp needle. After a large drop of blood has collected, the tip of the channeling member 26 is dipped into the blood drop, and capillary action will draw that blood up into the lumen 28 of the channeling member.

Since capillary action is determined by the viscosity of the liquid in question and the dimensions and composition of the material forming the capillary, the shape of the lumen 28 and the composition of the channeling member 26 can be selected so that the liquid to be tested will be drawn through capillary action into the lumen 28. The viscosity of the liquid to be tested will therefore determine the construction of the channeling member 26.

If the material to be tested is a liquid and it is held in a container, such as a beaker or test tube, the tip of the channeling member 26 can be dipped into the liquid. Liquid will then be drawn into the lumen 28 by capillary action.

Alternatively, drops of the liquid sample can be placed into the lumen 28 by dripping the liquid onto the base 27 of the sample collector 20. Again, capillary action will draw the liquid into the lumen 28. This approach may be preferred where the liquid to be tested is contained in a syringe or pipette.

If the material to be tested is highly viscous or even solid, the material can be dropped onto the base 27 of the sample collector 20.

Once the sample is held by sample collector 20, the sample is exposed to the buffer fluid held in buffer container 10, whether with or without agitation such as shaking. This requires the buffer fluid held within the buffer container 10 be allowed to flow out and come into contact with the sample.

With reference now to FIG. 1, this can be done by positioning the buffer container 10 in the sample collector 20 so that the membrane 18 of the buffer container 10 is pierced by the piercing edge 24 of the piercing member 23. If the buffer container 10 and the sample collector 20 have matching threads 19 and 29, respectively, this can be effected by positioning the buffer container 10 and sample collector 20 together so that the threads 19 and 29 are positioned for mating engagement. By then grasping the compressible grip 16 of the buffer container 10 and twisting, the threads 19 and 29 will engage and, owing to relative rotation therebetween, draw the buffer container 10 toward the base 27 of the sample collector 20. As the buffer container 10 moves toward the sample collector, the membrane 18 is pierced by the piercing edge 24 of the piercing member 23. Liquid in the buffer container 10 can then flow outward and downward under the influence of gravity and come into contact with the sample held in the sample container 20.

If desired, membrane 18 of the buffer container 10 can have a weakened portion (not shown) where it will, when stressed, fail first. The weakened portion may be positioned so that it will be contacted by the piercing edge of the piercing member 23. Such a weakened portion can be made by scoring, punching, etching and so forth. Now, after the sample collector 20 has been fitted into the sample collector and the buffer container turned to move the buffer container toward the sample collector 20, the piercing edge 24 strikes and ruptures that weakened portion. The buffer fluid can then flow out and mix with the sample. In another embodiment of the present invention, the buffer container can be rotated after piercing edge 24 strikes and ruptures the weaker portion, thereby further tearing the weakened portion and providing a larger opening for egress of the buffer fluid.

The sample collector 20 can be provided with a lug 39 which engages a matching notch (not shown) in the test strip container 50. This will keep the sample collector 20 from rotating within the test strip container 50 when the buffer container 10 joined thereto is twisted.

If desired, liquid flow out of the buffer container 10 can be hastened by squeezing the side walls 17, 17' of the compressible grip 16. This will deform and reduce the volume of buffer container 10, expelling the buffer fluid therefrom.

If the buffer container 10 has sealing rings 19 in place of threads, then the buffer container can be urged downward by pressure on the compressible grip 16. Again, the membrane 18 will be pierced, and the buffer fluid expelled to come into contact with the sample.

As an alternative construction, the sample collector 20 can be formed without a piercing member 23. Instead, the membrane 18 of the buffer container 10 can have a weakened portion (not shown) where it will, when stressed, fail first. The weakened portion can be made by scoring, punching, etching and so forth. Now, after the sample collector 20 has been fitted into the sample collector, the compressible grip 16 of the buffer container 10 is squeezed. This raises the pressure inside the buffer container 10 until the membrane 18 fails at the weakened portion. The buffer fluid can then flow out and mix with the sample, as already described.

The mixture of the buffer fluid and sample is then filtered by filter 30. This prevents the buffer fluid or the sample from contacting directly the test strip 40. By way of non-limiting example, if the sample being tested is blood, the filter 30 can separate out the white and red blood cells from the sample before the mixture of the buffer fluid and the sample contacts test strip 40.

By holding the sample testing device 1 upright, gravity will draw the mixture downward. Also, capillary action will draw the buffer fluid and sample into the pores of the filter 30. It will be appreciated that the rate at which liquid passes through the filter is affected by the composition and porosity of the filter 30. Reducing pore size will slow the rate of fluid flow, while increasing pore size will speed the fluid flow. Slowing fluid flow through the filter 30 may be necessary where it is desirable to have the buffer fluid and sample remain in contact for an extended period of time.

In addition to regulating the flow of buffer fluid and sample therethrough, filter 30 also blocks solid particles in the mixed buffer fluid and sample. This way, only liquid will reach the test strip 40. It will be appreciated that the size of the pores (not shown) of the filter 30 will determine which solid particles are prevented from reaching the test strip 40.

The filtered mixture of buffer fluid and sample, under the influence of capillary action and, possibly, gravity, is drawn downward through the filter 30 until some of the mixed liquid eventually comes into contact with the narrow end 44 of the test strip 40 held by the filter 30. Again, capillary action and, possibly, gravity, will draw the mixed buffer fluid and sample into the test strip 40.

With reference now to FIG. 1, the overall flow of buffer fluid and sample is in the direction of arrow A.

Once the mixed buffer fluid and sample have reacted with the test strip 40, which can take place in known fashion, the appearance of the test strip 40 may change, providing a visual indication of the result of the test being performed.

This result can be seen through either a window 55 in the test strip container 50, or the test strip container 50 itself if the test strip container 50 is transparent.

The testing system of the present invention may be employed to test subjects for a variety of medical conditions through use of the appropriate samples, buffer fluids and test strips. The manner of selecting a particular sample, buffer fluid and test strip to check for a condition of interest is itself known. Such medical conditions include, but are not limited to, hepatitis B, hepatitis C, HIV, tuberculosis, small pox, diphtheria and malaria. In addition, the instant testing system may be used to ascertain the presence of cardiovascular indicators in the blood of a subject thereby instantly alerting health care providers that the subject has recently suffered a cardiac event. Furthermore, the testing system may be used to determine the presence or absence of a drug in a subject's system. Examples of such drugs include, but are not limited to, alcohol, nicotine, and cocaine. The testing system may also be used by a law enforcement officer to readily ascertain if the blood alcohol content of a subject is above the legal limit. The testing system could also be used to identify the presence of various contaminants or pathogens. Examples of such pathogens or contaminants include, but are not limited to, anthrax, smallpox, botulism, Ebola virus, Legionnaire's disease, and so forth.

Thus, while there have been shown and described and pointed out fundamental novel features of the invention as applied to exemplary embodiments thereof, it would be understood that various omissions and substitutions and changes in the form and details of the disclosed invention may be made by those skilled in the art without departing from the spirit of the invention. It is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention that, as a matter of language, might be said to fall there between.

It also should be understood that the present invention is not intended to be limited to a method whose steps are performed in the order recited in the following claims. This invention encompasses the performance of those steps in other orders.

Thus, while there have been shown and described and pointed out fundamental novel features of the invention as applied to exemplary embodiments thereof, it would be understood that various omissions and substitutions and changes in the form and details of the disclosed invention may be made by those skilled in the art without departing from the spirit of the invention. It is the intention, therefore, to be limited only as indicated by the scope of the claim appended hereto.

What is claimed is:

1. A sample testing device, comprising:

a buffer container having an interior which receives a buffer fluid therein and a weakened portion;

a test strip having an end;

a filter holding the end of the test strip;

a test strip container having a receptacle dimensioned and disposed to accommodate said filter, so that when said filter is accommodated by said test strip container, the test strip is disposed in said receptacle;

a sample collector for holding a sample therein and which is shaped to receive said buffer container, said sample collector having a channeling member having a lumen, wherein when the buffer container is squeezed, the weakened portion fails and the buffer fluid in the interior of the buffer container contacts the sample and passes through the lumen to said filter, wherein as the buffer fluid flows through the lumen of the sample collector, the buffer fluid contacts the sample and then flows directly through the filter to the test strip.

2. The sample testing device of claim 1, wherein said test strip is oriented substantially perpendicular to said filter.

3. The sample testing device of claim 1, wherein said buffer container has a threaded outer surface and said sample collector has a threaded inner surface, the threaded outer surface engaging the threaded inner surface when the buffer container and the sample collector are joined.

4. The sample testing device of claim 1, wherein said buffer container has a projection and said sample collector has a depression, the projection engaging the depression when the buffer container and the sample collector are joined.

5. The sample testing device of claim 1, wherein a top portion of said buffer container is bellowed, and wherein when said top portion is compressed, at least a portion of the buffer fluid is expelled from the buffer container.

6. The sample testing device of claim 1, wherein the buffer fluid is sealed within said buffer container.

7. The sample testing device of claim 1, wherein said buffer container comprises a compressible grip, and wherein when said grip is compressed, at least a portion of the buffer fluid is expelled from the buffer container.

8. The sample testing device of claim 1, wherein said test strip container has a viewing window through which the test strip is visible.

9. The sample testing device of claim 1, wherein said test strip container comprises a cover and a body, and said cover and said body are joined together.

10. The sample testing device of claim 9, wherein said cover and said body are joined together in fluid-tight fashion.

11. The sample testing device of claim 1, wherein said test strip is oriented substantially below said filter when the device is positioned in an upright manner.

12. The sample testing device of claim 1, wherein said test strip is held by the filter so as not to be in contact with sides of said receptacle when the testing device is positioned in an upright manner.

13. A sample testing device, comprising:

a buffer container having an interior which receives a buffer fluid therein and a weakened portion;

a test strip having an end;

a filter holding the end of the test strip, the test strip positioned below the filter when the testing device is positioned in an upright manner;

a test strip container having a receptacle dimensioned and disposed to accommodate said filter, so that when said filter is accommodated by said test strip container, the test strip is disposed in said receptacle, the test strip being held by the filter so as not to be in contact with sides of said receptacle when the testing device is positioned in an upright manner;

a sample collector holding a sample between the buffer container and the filter, wherein when the weakened portion is caused to fail, then the buffer fluid flows into contact with the sample and then flows directly through the filter to the test strip.

* * * * *